US008147436B2

(12) United States Patent
Agrawal et al.

(10) Patent No.: US 8,147,436 B2
(45) Date of Patent: Apr. 3, 2012

(54) POWERED ORTHOSIS

(75) Inventors: Sunil Agrawal, Newark, DE (US); Sai Banala, Hamden, CT (US)

(73) Assignee: University of Delaware, Newark, DE (US)

( * ) Notice: Subject to any disclaimer, the term of this patent is extended or adjusted under 35 U.S.C. 154(b) by 1034 days.

(21) Appl. No.: 12/062,903

(22) Filed: Apr. 4, 2008

(65) Prior Publication Data

US 2008/0255488 A1 Oct. 16, 2008

Related U.S. Application Data

(60) Provisional application No. 60/922,216, filed on Apr. 6, 2007.

(51) Int. Cl.
*A61F 5/00* (2006.01)

(52) U.S. Cl. ............................................ 602/16; 602/23

(58) Field of Classification Search .................... 602/16, 602/23, 26–28, 19, 32–36; 128/882
See application file for complete search history.

(56) References Cited

U.S. PATENT DOCUMENTS 2,210,269 A 8/1940 Taylor
5,020,790 A 6/1991 Beard et al.
5,333,604 A 8/1994 Green
5,476,441 A * 12/1995 Durfee et al. .................. 602/23
6,039,707 A 3/2000 Crawford et al.
6,213,554 B1 4/2001 Marcoux et al.
6,666,796 B1 12/2003 MacReady
6,821,233 B1 11/2004 Colombo et al.
7,247,128 B2 7/2007 Oga
2003/0023195 A1 1/2003 Rahman et al.
2004/0049291 A1 3/2004 DeHarde et al.
2005/0043661 A1 2/2005 Nashner
2006/0241539 A1* 10/2006 Agrawal et al. ................ 602/23
2006/0293617 A1* 12/2006 Einav et al. .................... 601/33

FOREIGN PATENT DOCUMENTS

GB 1 406 420 A 9/1975
WO WO 94/09727 A 5/1994
WO WO 00/28927 A 5/2000

OTHER PUBLICATIONS

International Preliminary Report on Patentability dated Oct. 6, 2009.

(Continued)

*Primary Examiner* — Michael A. Brown
(74) *Attorney, Agent, or Firm* — RatnerPrestia

(57) ABSTRACT

A powered orthosis, adapted to be secured to a corresponding body portion of the user for guiding motion of a user, the orthosis comprising a plurality of structural members and one or more joints adjoining adjacent structural members, each joint having one or more degrees of freedom and a range of joint angles. One or more of the joints each comprise at least one back-drivable actuator governed by a controller for controlling the joint angle. The plurality of joint controllers are synchronized to cause the corresponding actuators to generate forces for assisting the user to move the orthosis at least in part under the user's power along a desired trajectory within an allowed tolerance. One embodiment comprises force-field controllers that define a virtual tunnel for movement of the orthosis, in which the forces applied to the orthosis for assisting the user may be proportional to deviation from the desired trajectory.

18 Claims, 11 Drawing Sheets

OTHER PUBLICATIONS

Abbas Fattah, Sunril K. Agrawal; "On the Design of a Passive Orthosis to Gravity Balance Human Legs"; Professor; vol. 127, Jul. 2005; Journal of Mechanical Design; pp. 802-808.

Sunril K. Agrawal; Sai K. Banala; "Gait Rehabilitation With an Active Leg Orthosis"; Proceedings of IDETC/CIE 2005; pp. 1-7.

Sunil K. Agrawal; Abbas Fattah; "Theory and Design of an Orthotic Device for Full or Partial Gravity-Balancing of a Human Leg During Motion"; IEEE Transactions on Neural Systems and Rehabilitation Engineering, vol. 12, No. 2, Jun. 2004; pp. 157-165.

Sai K. Banala, Alexander Kulpe; Sunil K. Agrawal; "A Powered Leg Orthosis for Gait Rehabilitation of Motor-Impaired Patients"; 2007 IEEE International Conference on Robotics and Automation, Roma Italy, Apr. 10-14, 2007; pp. 4140-4145.

Robert Riener, Maurizio Ferrarin, Esteban Enrique Pavan, Carlo Albino Frigo; "Patient-Driven Control of FES-Supported Standing Up and Sitting Down: Experimental Results"; IEEE Transactions of Rehabilitation Engineering, vol. 8, No. 4, Dec. 2000; pp. 523-529.

Robert Reiner, Lars Lunenburger, Saso Jezernik, Martin Anderschitz, Gery Colombo, and Volker Dietz; "Patient-Cooperative Strategies for Robot-Aided Treadmill Training: First Experimental Results"; IEEE Transactions on Neural Systems and Rehabilitative Engineering; vol. 13, No. 3, Sep. 2005; pp. 380-394.

R.Ekkelenkamp, J. Veneman; H Van Der Kooij; "Lopes: a lower extremity powered exoskeleton"; 2007 IEEE International Conference on Robotics and Automation Roma, Italy, Apr. 10-14, 2007; pp. 3132-3133.

Robert Reiner & Thomas Edrich; "Identification of passive elastic joint moments in the lower extremities"; Journal of BioMechanics; 1999; pp. 539-544.

Michael Bernhardt, Martin Frey, Gery Colombo, Robert Reiner; "Hybrid Force-Position Control Yields Cooperative Behaviour of the Rehabilitation Robot Lokomat"; Proceedings of the 2005 IEEE 9$^{th}$ International Conference of Rehabilitation Robotics; Jun. 28-Jul. 1, 2005, Chicago, IL, USA; pp. 536-539.

Saso Jezernik, Gery Colombo, Manfred Morari; "Automatic Gait-Pattern Adaptation Algorithms for Rehabilitation With a 4-DOF Robotics Orthosis"; IEEE Transactions in Robotics and Automation; vol. 20, No. 3, Jun. 2004; pp. 574-582.

D. Aoyagi, W.E. Ichinose, J.E. Bobrow, S,J. Harkema; "An Assistive Robotic Device That Can Synchronize to the Pelvic Motion During Human Gait Training"; Proceedings of the 2005 IEEE 9$^{th}$ International Conference of Rehabilitation Robotics; Jun. 28-Jul. 1, 2005, Chicago, IL, USA; pp. 565-568.

Lance L. Cai, Andy J. Fong, Yongqiang Liang, Joel Burdick, V. Reggie Edgerton; "Assist-as-needed Training Paradigms for Robotic Rehabilitation of Spinal Cord Injuries"; Proceedings of the 2006 IEEE International Conference of Robotics and Automation; Orlando, Florida-May 2006; pp. 3504-3511.

Robert Reiner, Martin Frey, Michael Bernhardt, Tobias Nef Gery Colombo; "Human-Centered Rehabilitation Robotics"; Proceedings of the 2005 IEEE 9$^{th}$ International Conference of Rehabilitation Robotics; Jun. 28-Jul. 1, 2005, Chicago, IL, USA; pp. 319-322.

Stephen Pledgie, Kenneth E. Barner, Member IEEE, Sunil K. Agrawal, and Tariq Rahman; "Tremor Suppression Through Impedance Control"; IEEE Transaction on Rehabilitation Engineering; vol. 8, No. 1, Mar. 2000; pp. 53-59.

Sunil K. Agrawal, Abbas Fattah; "Design of an Orthotic Device for Full or Partial Gravity-Balancing of a Human Upper Arm During Motion"; Proceedings of the 2003 IEEE/RSJ Internation Conference on Intelligent Robots and Systems, Las Vegas, Nevada-Oct. 2003; pp. 2841-2846.

Abhishek Agrawal, Sunil K. Agrawal; "Design of Gravity balancing leg orthosis using non-zero free length springs"; Mechanism and Machine Theory; Science Direct; pp. 693-709.

Abbas Fattah, Sunil K. Agrawal, Glenn Catlin, John Hamnett; "Design of a Passive Gravity-Balanced Assistive Device for Sit-to-Stand Tasks"; vol. 128, ASME; Sep. 2006; pp. 1122-1129.

International Search Report for International Application No. PCT/US08/04330 mailed Jul. 25, 2008.

International Search Report for International Application No. PCT/US08/04319 mailed Jul. 25, 2008.

U.S. Appl. No. 12/062,885 of Mankala et al. filed Apr. 4, 2008.

U.S. Appl. No. 11/113,729 of Agrawal et al. filed Apr. 25, 2005.

U.S. Appl. No. 11/409,163 of Agrawal et al. filed Apr. 21, 2006.

Sunil K. Agrawal, Abbas Fattah, Sai Banala; "Design and Prototype of a Gravity-Balanced Leg Orthosis"; International Journal of HWRS; vol. 4, No. 3; Sep. 2003; pp. 13-16.

Sai K. Banala, Sunil K. Agrawal, Abbas Fattah, Katherine Rudolph, John P. Scholz; "A Gravity Balancing Leg Orthosis for Robotic Rehabilitation"; Proceedings of the 2004 IEEE International Conference on Robotics & Automation; Apr. 2004; pp. 2474-2479.

Abbas Fattah, Ph.D. et al.; "Design of a Gravity-Balanced Assistive Device for Sit-to-Stand Tasks" ASME Journal; Proceedings of DETC '04 ASME 2004 Design Engineering Technical Conferences Sep. 28-Oct. 2, 2004; Salt Lake City, Utah, USA; pp. 1-7.

Roman Kamnik, et al.; "Robot Assistive Device for Augmenting Standing-Up Capabilities in Impaired People"; journal; Oct. 2003; pp. 3606-3611; Proceedings of the 2003 IEEE/RSJ International Conference on Intelligent Robots and Systems, Las Vegas, NV; USA.

Michael Peshkin, et al.; "KineAssist: A Robotic Overground Gait and Balance Training Device"; Proceedings of the 2005 IEEE 9$^{th}$ International Conference on Rehabilitation Roboticss; 2005; pp. 241-246; Chicago PT LLC, Evanston, IL; USA.

Roman Kamnik et al.; "Rehabilitation Robot Cell for Multimodal Standing-Up Motion Augmentation"; article; Apr. 2005; pp. 2289-2294; Proceedings of the 2005 IEEE International Conference on Robotics and Automation; Barcelona, Spain; Spain.

T. Bajd et al.; "Standing-Up of a Healthy Subject and a Paraplegic Patient"; article; 1982; pp. 1-10; vol. 15, No. 1; J. Biomechanics, Great Britain.

N de N Donaldson et al.; "FES Standing: Control by Handle Reactions of Leg Muscle Stimulation" (CHRELMS); Dec. 1996; pp. 280-284; vol. 4, No. 4; IEEE Transactions on Rehabilitation Engineering; New York, NY; USA.

* cited by examiner

POWERED ORTHOSIS

CROSS-REFERENCE TO RELATED APPLICATIONS

This application claims priority to U.S. Provisional Patent Application Ser. No. 60/922,216, filed Apr. 6, 2007, incorporated herein by reference.

STATEMENT REGARDING FEDERALLY SPONSORED RESEARCH

The U.S. Government has a paid-up license in this invention and the right in limited circumstances to require the patent owner to license others on reasonable terms as provided for by the terms of NIH Grant #1 RO1 HD38582-01A2, awarded by the National Institutes of Health.

FIELD OF THE INVENTION

The present invention relates to an apparatus for assisting a user to move an extremity in a desired trajectory, such as an apparatus for applying forces to a user's leg to assist in gait rehabilitation of a patient with walking disabilities.

BACKGROUND OF THE INVENTION

Neurological injury, such as hemiparesis from stroke, results in significant muscle weakness or impairment in motor control. Patients experiencing such injury often have substantial limitations in movement. Physical therapy, involving rehabilitation, helps to improve the walking function. Such rehabilitation requires a patient to practice repetitive motion, specifically using the muscles affected by neurological injury. Robotic rehabilitation can deliver controlled repetitive training at a reasonable cost and has advantages over conventional manual rehabilitation, including a reduction in the burden on clinical staff and the ability to assess quantitatively the level of motor recovery by using sensors to measure interaction forces and torques in order.

Currently, available lower extremity orthotic devices can be classified as either passive, where a human subject applies forces to move the leg, or active, where actuators on the device apply forces on the human leg. One exemplary passive device is a gravity balancing leg orthosis, described in U.S. patent application Ser. No. 11/113,729 (hereinafter "the '729 application"), filed Apr. 25, 2005, and assigned to the assignee of the present invention, incorporated herein by reference. This orthosis can alter the level of gravity load acting at a joint by suitable choice of spring parameters on the device. This device was tested on healthy and stroke subjects to characterize its effect on gait.

Passive devices cannot supply energy to the leg, however, and are therefore limited in their ability compared to active devices. Exemplary active devices include T-WREX, an upper extremity passive gravity balancing device; the Lokomat® system, which is an actively powered exoskeleton designed for patients with spinal cord injury for use while walking on a treadmill; the Mechanized Gait Trainer (MGT), a single degree-of-freedom powered machine that drives the leg to move in a prescribed gait pattern consisting of a foot plate connected to a crank and rocker system that simulates the phases of gait, supports the subjects according to their ability, and controls the center of mass in the vertical and horizontal directions; the AutoAmbulator, a rehabilitation machine for the leg to assist individuals with stroke and spinal cord injuries and designed to replicate the pattern of normal gait; HAL, a powered suit for elderly and persons with gait deficiencies that takes EMG signals as input and produces appropriate torque to perform the task; BLEEX (Berkeley Lower Extremity Exoskeleton), intended to function as a human strength augmenter; and PAM (Pelvic Assist Manipulator), an active device for assisting the human pelvis motion. There are also a variety of active devices that target a specific disability or weakness in a particular joint of the leg.

A limiting feature of existing active devices, however, is that they move a subject through a predestined movement pattern rather than allowing the subject to move under his or her own control. The failure to allow patients to self-experience and to practice appropriate movement patterns may prevent changes in the nervous system that are favorable for relearning, thereby resulting in "learned helplessness," which is sub-optimal. Fixed repetitive training may cause habituation of the sensory inputs and may result in the patient not responding well to variations in these patterns. Hence, the interaction force between the human subject and the device plays a very important role in training. For effective training, the involvement and participation of a patient in voluntarily movement of the affected limbs is highly desirable. Therefore, there is a need in the art for devices that assist the patient as needed, instead of providing fixed assistance.

SUMMARY OF THE INVENTION

One aspect of the invention comprises a powered orthosis adapted to be secured to a corresponding body portion of a user for guiding motion of the user. The orthosis comprises a plurality of structural members and one or more joints adjoining adjacent structural members. Each joint has one or more degrees of freedom and a range of joint angles. One or more of the joints comprises at least one back-drivable actuator governed by at least one controller for controlling the joint angle. The one or more joint actuator controllers are synchronized to cause the corresponding joint actuators to generate forces for assisting the user to move the orthosis at least in part under the user's power along a desired trajectory within an allowed tolerance. The joint controllers may comprise set-point controllers or force-field controllers. In an embodiment in which the joint controllers comprise force-field controllers that define a virtual tunnel for movement of the orthosis, the forces applied to the orthosis for assisting the user are proportional to deviation from the desired trajectory, and may include tangential forces along the trajectory and normal forces perpendicular to the trajectory. Tangential forces are inversely proportional to the deviation from the desired trajectory, whereas the normal forces are directly proportional to the deviation from the desired trajectory.

Another aspect of the invention comprises a method for training a user to move a portion of the user's body in a desired trajectory. The method comprises securing the user to an orthosis as described above, and causing the synchronized joint controllers to operate the corresponding actuators to generate forces for assisting the user to move the orthosis at least in part under the user's power along a desired trajectory within an allowed tolerance. The method may further comprise providing visual feedback to the user that shows a relationship between the desired trajectory and an actual trajectory followed by the orthosis in response to movement by the user. In one embodiment, the method may comprise a method for rehabilitation of a patient with impaired motor control.

In one embodiment, the orthosis is a leg orthosis comprising a frame adapted to support at least a portion of the weight of the orthosis and the user, a trunk connected to the frame at one or more trunk joints, a thigh segment connected to the trunk at least a hip joint, a shank segment connected to the thigh segment at a knee joint, and optionally, a foot segment attached to the shank segment at an ankle joint. The hip joint may have at least one degree of freedom in the saggital plane governed by a first actuator and the knee joint may have at least one degree of freedom governed by a second actuator. A method of using such an embodiment may comprise training the user to adopt a desired gait.

Still another aspect of the invention comprises a method for training a healthy user to adopt a desired trajectory for a body motion, the method comprising securing the user to an orthosis as described herein and causing the synchronized joint controllers to operate the corresponding actuators to generate forces for assisting the user to move the orthosis at least in part under the user's power along the desired trajectory within an allowed tolerance.

BRIEF DESCRIPTION OF THE DRAWINGS

The invention is best understood from the following detailed description when read in connection with the accompanying drawings. It is emphasized that, according to common practice, various features/elements of the drawings may not be drawn to scale. On the contrary, the dimensions of the various features/elements may be arbitrarily expanded or reduced for clarity. Moreover, in the drawings, common numerical references are used to represent like features/elements. Included in the drawing are the following figures.

DETAILED DESCRIPTION OF THE INVENTION

Figure 1A:
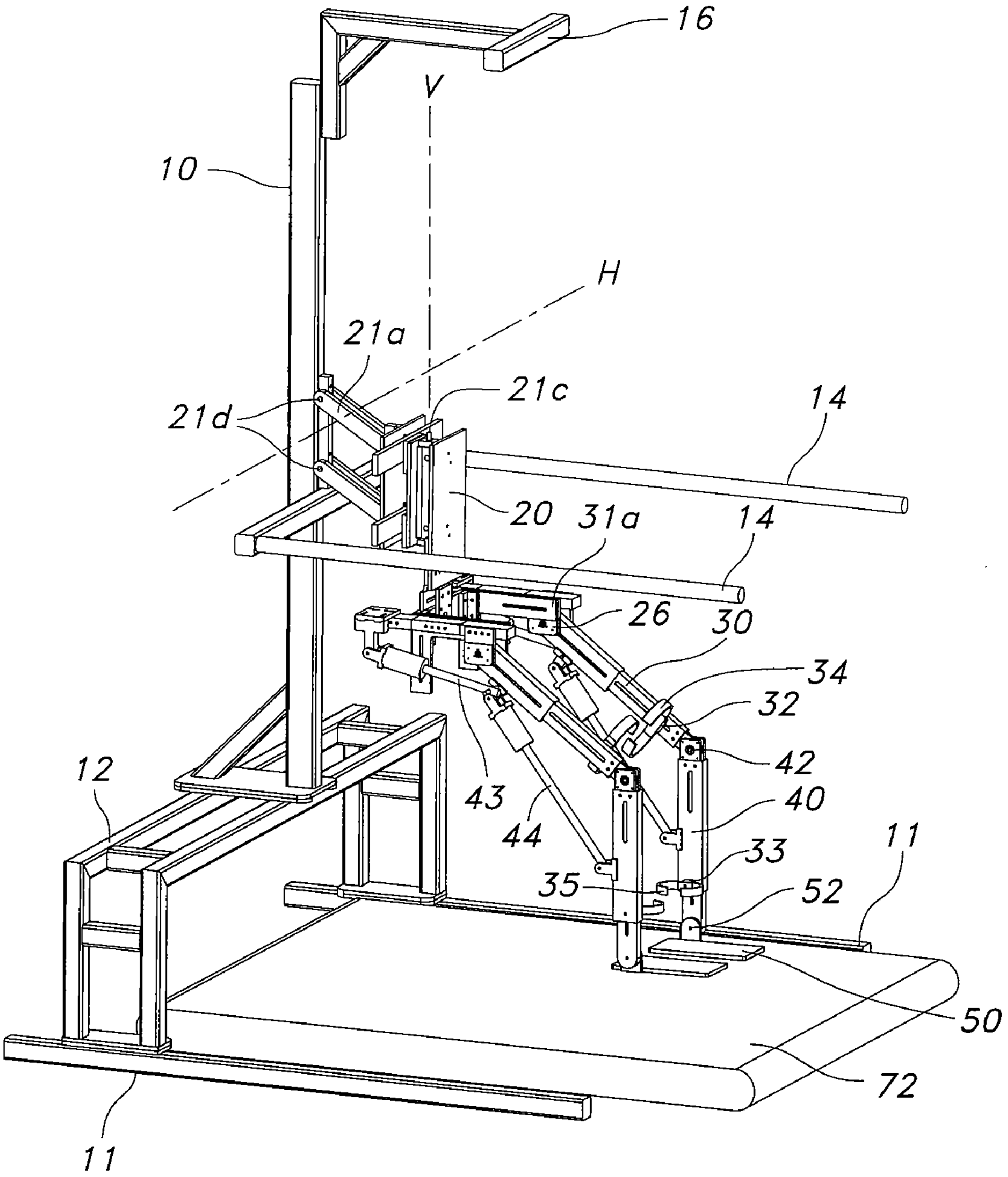
FIG. 1A is a side perspective schematic drawing of an exemplary powered leg orthosis in accordance with the invention.
Figure 1B:
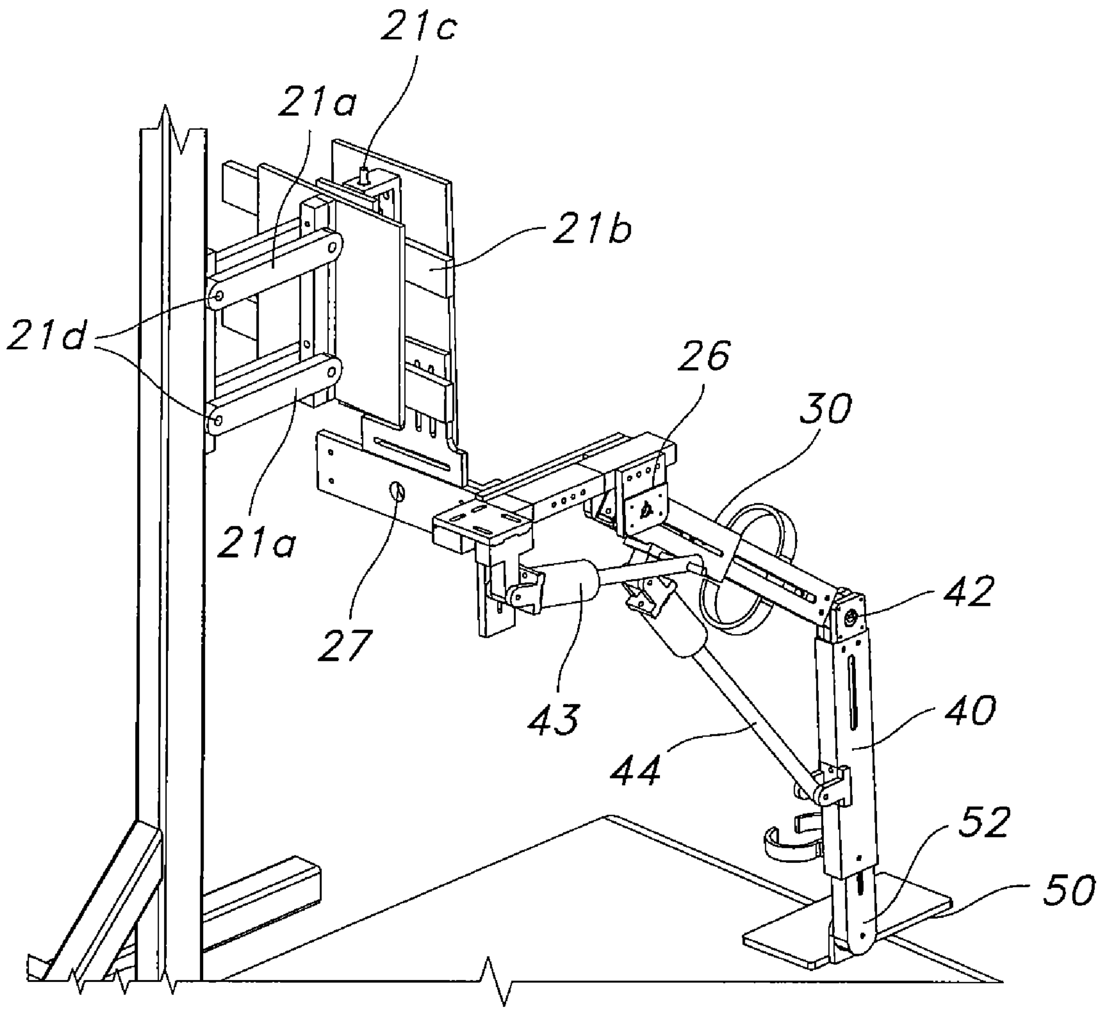
FIG. 1B is a detailed view of selected joints from the schematic of FIG. 1A.

Referring now to the drawings, an exemplary powered leg orthosis is schematically illustrated in FIGS. 1A-1B. The exemplary orthosis is based upon the prototype passive Gravity Balancing Leg Orthosis described in the '729 application. The overall setup comprises frame 10, trunk 20, thigh segment 30, shank segment 40, and foot segment 50. Frame 10 takes the weight of the entire device. Trunk 20 is connected to the frame through a plurality of trunk joints 21*a*-21*d* having four degrees-of-freedom. These degrees-of-freedom are vertical translation provided by parallelogram mechanism 21*a* having revolute joints 21*d*, lateral translation via slider-block and slider-bar 21*b*, rotation about vertical axis V at revolute joint 21*c*, and rotation about horizontal axis H perpendicular to sagittal plane S at revolute joints 21*d*. User 22 is secured to trunk 20 of the orthosis with a hip brace 24.

Thigh segment 30 has two degrees-of-freedom with respect to trunk of the orthosis: translation in the sagittal plane along hip joint 26 and abduction-adduction about joint 27, shown in FIG. 1B. The thigh segment 30 may be telescopically adjustable to match the thigh length of a human subject. Shank segment 40 has one degree-of-freedom with respect to the thigh segment 30 about knee joint 42, and may also be telescopically adjustable. Foot segment 50, comprising a shoe insert, is attached to the shank of the leg with a one degree-of-freedom ankle joint 52. Foot segment 50 comprises a structure that allows inversion-eversion motion of the ankle. The ankle segment described above is used when a human subject is in the device. At other times, such as during testing or setup, for example, a dummy leg may be used that does not have a foot segment.

Hip joint 26 in the sagittal plane and knee joint 42 are actuated using a first and second linear actuator 43 and 44, respectively. These linear actuators 43, 44 have encoders built into them for determining the joint angles. The physical interface between the orthosis and the subject leg is through two force-torque sensors: a first sensor 32 mounted between thigh segment 30 of the orthosis and the thigh user interface 34, and a second sensor 33 mounted between shank segment 40 of the orthosis and the shank user interface 35.

As shown in FIG. 1A, frame 10 may comprise a base 12, a pair of arm supports 14, and an overhead weight support 16 from which some or all of the user's weight may be supported for users who need such assistance. A treadmill 72 is provided underneath the user between legs 11 of base 12. Although shown with a treadmill 72 and static frame 10, it should be noted that other configurations (not shown) may comprise a portable frame that allows the user to walk on solid ground rather than on a treadmill. Such portable configurations may comprise arm supports, such as in the form of a walker that rolls along with the user, or may not have such supports. Furthermore, while the design noted in FIG. 1A shows two powered leg orthosis, other embodiments may have only a single powered orthosis, as is shown in FIG. 1B, depending upon the needs of the user and purpose of the configuration.

Figure 2:
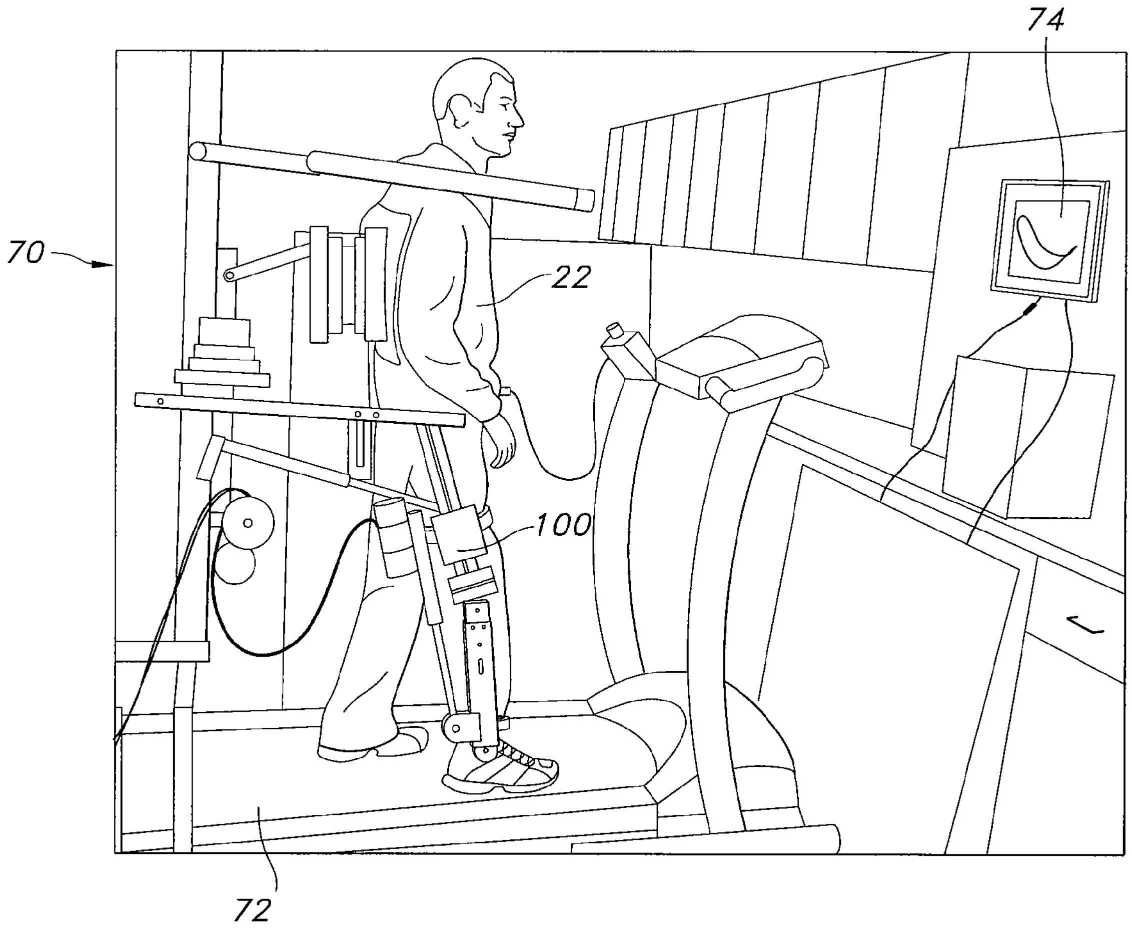
FIG. 2 is an illustration of an overall gait training setup for use with the orthosis of FIG. 1.

An exemplary overall gait training setup 70 is shown in FIG. 2. The user 22 walks on a treadmill 72 with orthosis 100 on the right leg only. The display 74 in front of the subject provides visual feedback of the executed gait trajectory. The visual display can be used to show the gait trajectory in real time during training. The subject's performance can be recorded from each training session. The trajectory can be recorded using either joint angles (in joint space) or the foot coordinates (in foot space). This motorized orthosis is architecturally similar to the passive leg described in the '729 application. A walker with a harness to the trunk may be used to keep the subject stable on the treadmill during exercise.

Referring now to FIG. 1B, controllers connected to linear actuators 43 and 44 are used to create desired force fields on the moving leg as discussed in more detail below. The goal of these controllers is to assist or resist the motion of the leg at least in part under the user's power along a desired trajectory within an allowable tolerance, as needed, by applying force-fields around the leg. In this way, the user is not restricted to a fixed repetitive trajectory. Various types of controller methodologies may be used, including trajectory tracking controllers, set-point controllers, and force field controllers. Trajectory tracking controllers move the leg in a fixed trajectory, which is often not the most desirable way for gait training. Set-point control and force-field control use the concept of assistive force as needed, which is a functionality believed to be more desirable.

Trajectory Tracking Controller

In the trajectory tracking controller, desired trajectory $\Theta_d(t)$ is a prescribed function of time, whereas in set-point PD control, a finite number of desired set-points are used. The current set-point moves to the next point only when the current position is within a given tolerance region of the current set-point. Both the trajectory tracking controller and set-point PD controller use feedback linearized PD control in joint space. In a force-field controller, the forces are applied at the foot to create a tunnel or virtual wall-like force field around the foot. The patient using the orthosis for rehabilitation is then asked to move the leg along this tunnel. The set-points for the controller are chosen such that the density of points is higher in the regions of higher path curvature in the foot space.

To meet the challenging goal of using a light weight motor and at the same time requiring the motor to provide sufficient torque, a linear actuator driven by an electric motor may be used. Linear actuators typically cannot be back-driven, meaning that it is very hard to make the linear actuator move merely be applying force on it. This happens because the frictional and damping force in the lead screw of the motor gets magnified by its high transmission ratio. By using a suitable friction compensation technique, however, the motor can be made backdrivable.

Backdrivability of actuators is desirable for using force based control, because it makes it easier for the subject to move his or her leg without sizable resistance from the device. Exemplary friction compensation methods may comprise model based compensation, in which frictional forces are fed forward to the controller using a friction model obtained from experiments, or load-cell based compensation, in which load-cells are aligned with the lead screw of the linear actuator along with a fast PI controller.

Figure 3:
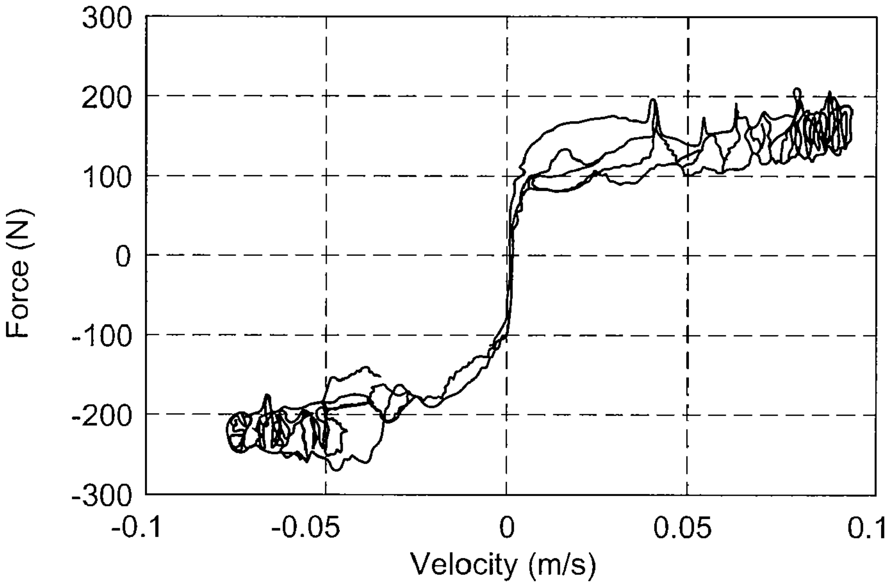
FIG. 3 is graph of exemplary frictional force data collected by experiment from a motor as a function of its linear velocity, which is illustrative of the type of data that can be incorporated into a friction model for calculation of friction compensation.

For feed-forward friction compensation, a good friction model is required. Frictional force data may be collected by experiment from a motor as a function of its linear velocity, such as is shown in FIG. 3. This behavior can be approximated with the equation:

$$F_{friction}=K_{fs}\mathrm{sign}(\dot{x})+K_{fd}\dot{x}$$

where $\dot{x}$ is the linear velocity of the motor and $K_{fs}$ and $K_{fd}$ are constants.

The friction model is only an approximation and the actual friction has a complicated dependency on the load applied to the motor and on the configuration of the device. Some of the problems of model based friction compensation can be overcome by using a load cell in series and a fast PI controller with a suitable time constant.

Figure 4:
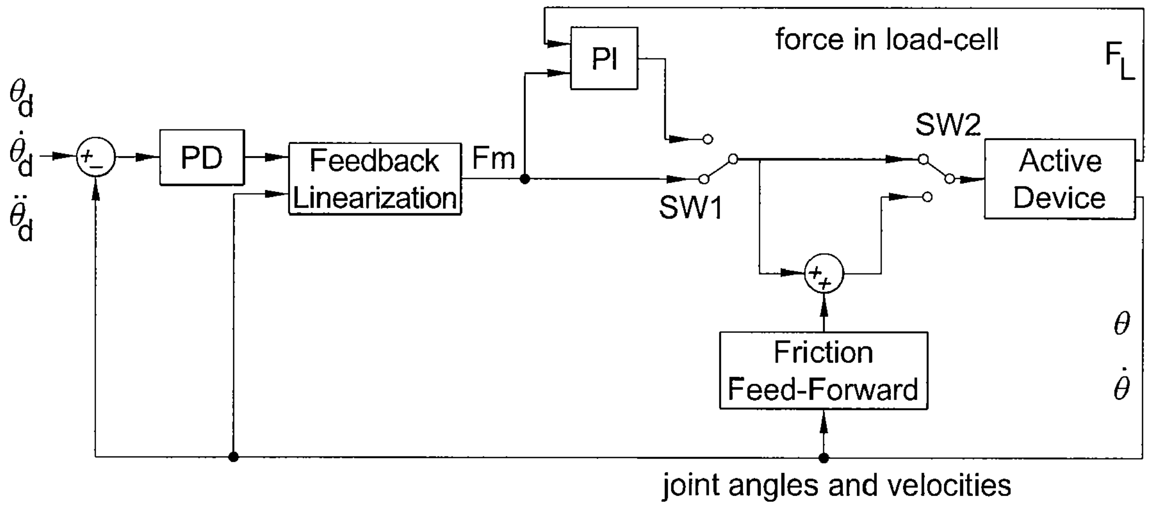
FIG. 4 is a schematic diagram of an exemplary PD controller.

Trajectory tracking controller tracks the desired trajectory using a feedback linearized PD controller. This controller is simple and is robust to friction with higher feedback gains. When used with friction compensation, small feedback gains can be used. FIG. 4 shows a schematic of an exemplary trajectory tracking PD control, in which $\Theta$ represents the joint angle, $\Theta_d$ the desired trajectory, and $F_L$ the force measured by a load-cell. Switch SW1 turns on the load-cell based friction compensation and switch SW2 turns on the model-based friction compensation. Thus, the user may choose to use load-cell based friction compensation, which compensates whenever the load detects the user exerting a net force on the orthosis in the direction of travel indicating, or model-based compensation, which provides friction compensation along the trajectory based upon the direction and velocity of travel as derived from modeling. The model-based compensation tends to be more anticipatory, whereas the load-cell-based compensation is based more on feedback. A combination of compensation techniques may also be used, meaning that the model generally provides the compensation except when the load cell detects that additional compensation is needed. This same schematic applies to the set point controller, described herein later, except that for the set point controller $\dot{\theta}_d$ and $\ddot{\theta}_d$ are zero.

In this trajectory tracking controller, the desired trajectory in terms of joint angles is a function of time, $\Theta_d=\Theta_d(t)$. The desired trajectory may be obtained from healthy subject walking data, using experiments with a passive device. The equations of motion for the device are given below. Note that the frictional terms are not mentioned here, as they are assumed to be compensated using one of the two friction compensation methods outlined above.

Figure 5:
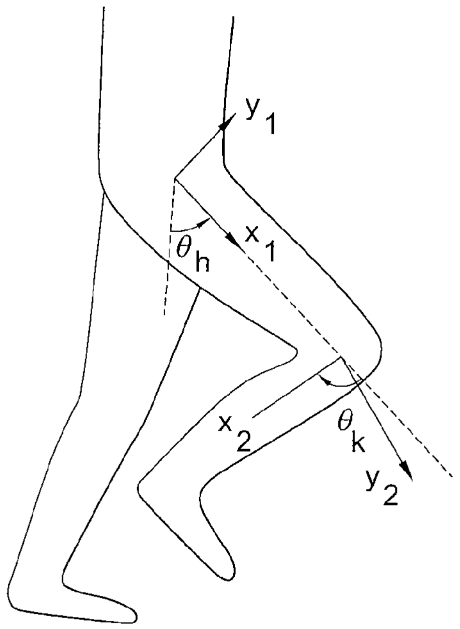
FIG. 5 is a schematic illustration of the anatomical joint angle convention used in the equations discussed herein.

Equations of Motion:

$$M\ddot{\theta}+C(\dot{\theta},\theta)\dot{\theta}+G(\theta)=\tau, \tag{1}$$

where $\theta=[\theta_h\theta_k]^T$ shown in FIG. 5.

Control Law is given by:

$$\tau=M(\ddot{\theta}_d+K_d\dot{\theta}_c+K_p\theta_e)+C(\dot{\theta},\theta)\dot{\theta}+G(\theta),\text{ where }\theta_c=\theta_d-\theta$$

This law linearizes the equations to an exponentially stable system:

$$\ddot{\theta}_c+K_d\dot{\theta}_c+K_p\theta_e=0 \tag{2}$$

where $$K_p=\begin{pmatrix}K_{p1} & 0\\ 0 & K_{p2}\end{pmatrix}\text{ and }K_d=\begin{pmatrix}K_{d1} & 0\\ 0 & K_{d2}\end{pmatrix}$$

are positive matrices.

Experimental Results

One way to use small feedback gains is to use friction compensation. If desired trajectory is a function of time, the error in any joint may keep increasing if that joint is prevented from moving. This may cause the force in the motor of that joint to increase with the error. One set of experimental results found that applying external forces caused forces in the hip motor to almost double. This increase in forces when the subject wishes not to move the leg may not be safe or suitable for training.

Set-Point PD Controller

A set-point PD controller is similar to trajectory tracking controller except that there are a finite number of desired trajectory points $((\theta_{d1},\theta_{d2}, \ldots ,\theta_{dn})$ and desired trajectory velocities and accelerations are set to zero $(\dot{\theta}_d=\ddot{\theta}_d=0)$. The controller takes the device to the current set-point. Once the current position of the device is close to the current set-point, the current set-point is switched to the next set-point. If the number of set-points is small, the device motion is jerky. By choosing a sufficient number of points, however, the leg trajectory can be made smooth.

One of the advantages of set-point PD controller over a trajectory tracking controller is that if the human subject wishes to stop the device, the forces on the leg stays within limit, and the set-point will not change.

The control law is same as the one used in the trajectory tracking PD controller with desired trajectory velocities and accelerations set to zero $(\dot{\theta}_d=\ddot{\theta}_d=0)$. The current setpoint $\theta_{cur}=\theta_1$ advances to the next set-point $\theta_{i+1}$ if $\|\theta-\theta_{cur}\|=\epsilon$, where $\epsilon$ is the allowed tolerance.

Simulated and Experimental Results with Set-Point Controller

Simulations and experiments were performed for three sets of feedback gains chosen such that the natural frequency of the system described in Eq. (2) was $\omega_n=10.12$ and $\xi=\{3.2, 0.5\}$. The simulation essentially comprised coupling a model of a human leg and body dynamics to a model of the powered orthosis and controllers, and running the models together to predict how the system would work on a human subject. For greater values of damping, it was found that the joint trajectories lied inside the desired trajectory due to slowing effects of damping. At lesser values of damping, it was found that the trajectories fluctuated around the desired trajectory due to faster speeds and overshoots.

Force-Field Controller

Figure 6:
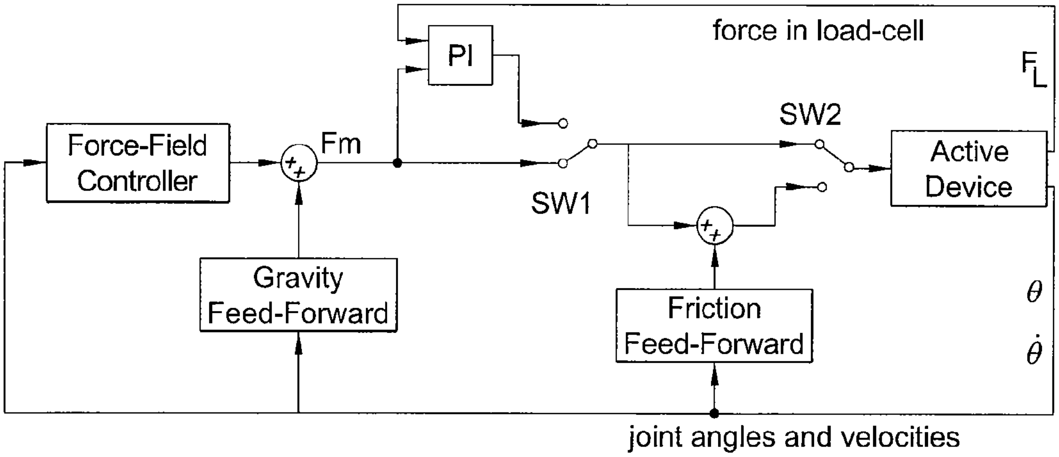
FIG. 6 is a schematic diagram of an exemplary force field controller.
Figure 7:
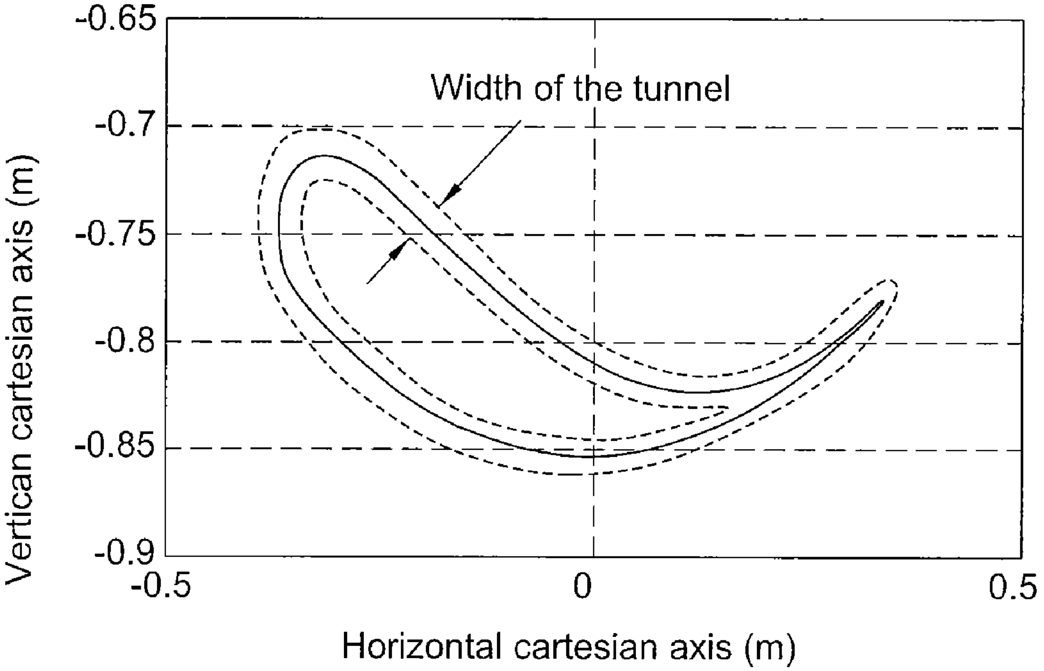
FIG. 7 is an exemplary Cartesian plot of foot trajectory and the corresponding virtual tunnel associated with an exemplary force field controller.

The goal of a force-field controller is to create a force field around the foot in addition to providing damping to it. This force field is shaped like a “virtual tunnel” around the desired trajectory. FIG. 6 shows the basic structure of the controller, wherein FL is the force measured by the load-cell. Switch SW1 turns on sensor-based friction compensation and switch SW2 turns on model-based friction compensation, as described above with respect to the PD controller. The force-field controller also uses gravity compensation to help the human subject. This assistance can be reduced or completely removed if required. FIG. 7 shows a typical shape of the virtual tunnel walls (dashed lines) around the desired trajectory (solid line) for a cartesian plot of the foot in the trunk reference frame, with the origin set at the hip joint.

Figure 8:
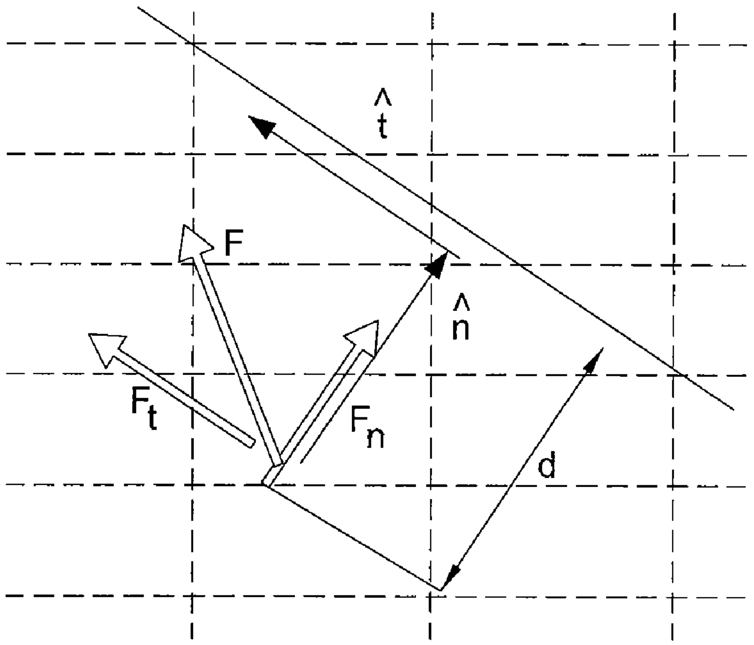
FIG. 8 is a schematic diagram of forces normal and tangential to the foot trajectory.

Because the virtual tunnel is used to guide the foot of the subject, the forces are applied on the foot, as illustrated in part in FIG. 8. These forces are a combination of tangential force $(F_t)$ along the trajectory, normal force $(F_n)$ perpendicular to the trajectory, which are proportional to a deviation from the desired trajectory, and damping force $(F_d)$ (not shown). The controller may be designed such that this normal component keeps the foot within the virtual tunnel. The tangential force provides the force required to move the foot along the tunnel in forward direction and is inversely proportional to the deviation from the desired trajectory. The normal force is directly proportional to the deviation from the desired trajectory. The damping force minimizes oscillations, as discussed previously.

Where P is the current position of the foot in the Cartesian space in the reference frame attached to trunk of the subject, N is the nearest point to P on the desired trajectory, $\hat{n}$ is the normal vector from P to N, and $\hat{t}$ is the tangential vector at N along the desired trajectory in forward direction, the force F on the foot is defined as:

$$F=F_t+F_n+F_d \tag{3}$$

$$F_t=K_{Ft}(1-d/D_t)\hat{t},\text{ if } d/D_t<1$$

$$F_t=0,\text{ otherwise} \tag{4}$$

where $F_t$ is the tangential force, $F_n$ is the normal force and $F_d$ is the damping force. The tangential force $F_t$ is defined as:

$$F_n=\left(\frac{d}{D_n}\right)^{2(n+1)}\hat{n} \tag{5}$$

The damping force $F_d$ on the foot to reduce oscillations is given by:

$$F_d=-K_d\dot{x} \tag{6}$$

where $K_{Ft}$. $D_t$. $D_n$ and $K_d$ are constants, d is the distance between the points P and N, and $\dot{x}$ is the linear velocity of the foot.

Figure 9A:
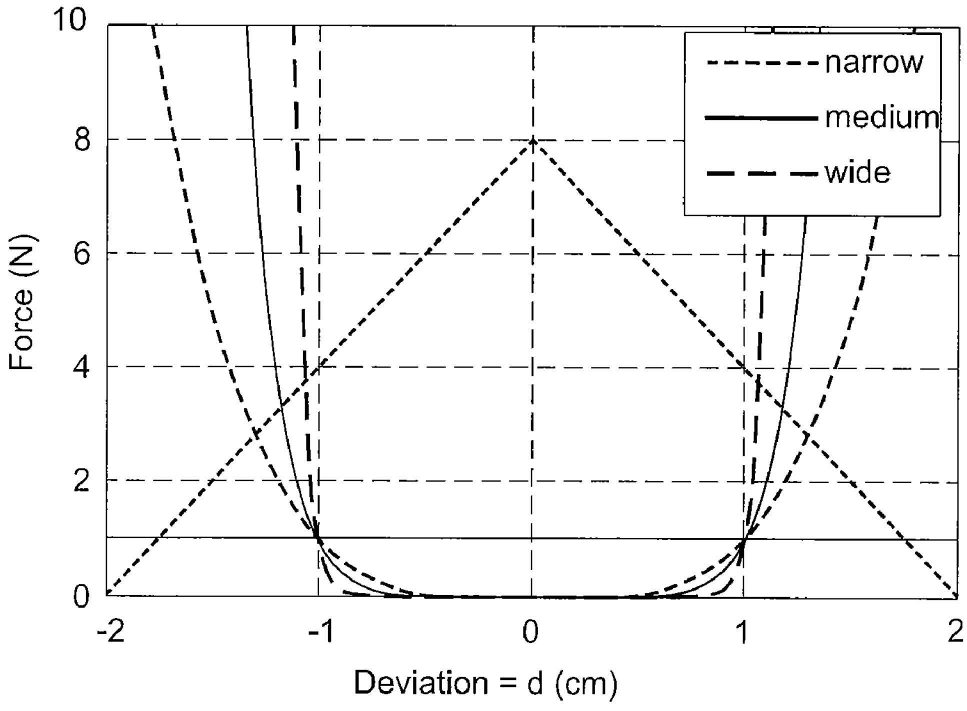
FIG. 9A is a plot of normal (U-shaped) and tangential (inverted V-shaped) force profiles as a function of distance from the center of the tunnel for different force field parameters (n).
Figure 9B:
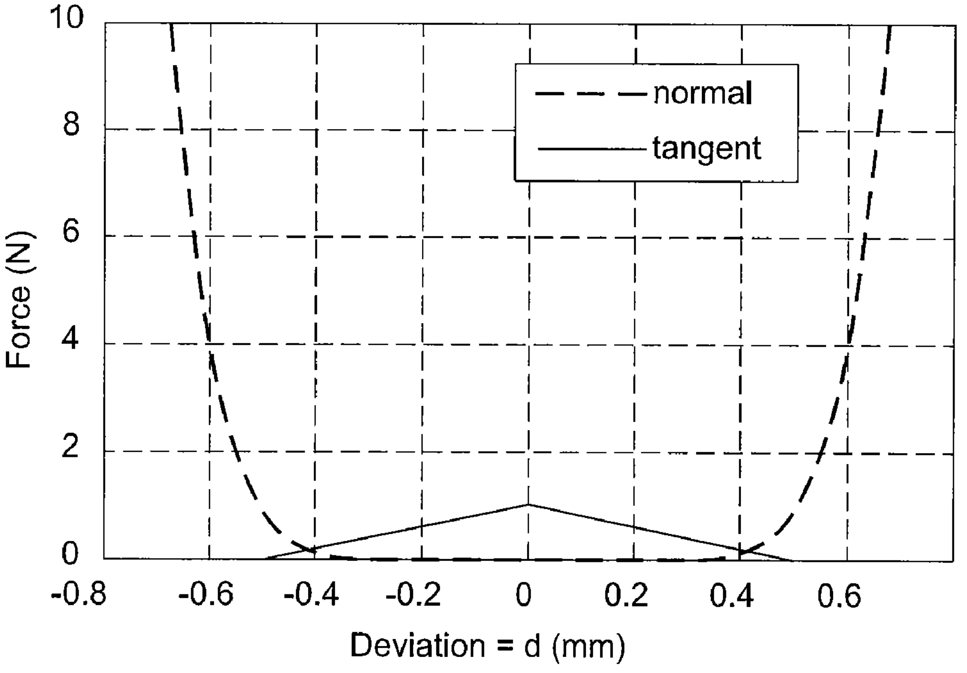
FIG. 9B is a plot of normal and tangential force profiles as a function of distance from the center of the tunnel for a relatively narrow tunnel.
Figure 9C:
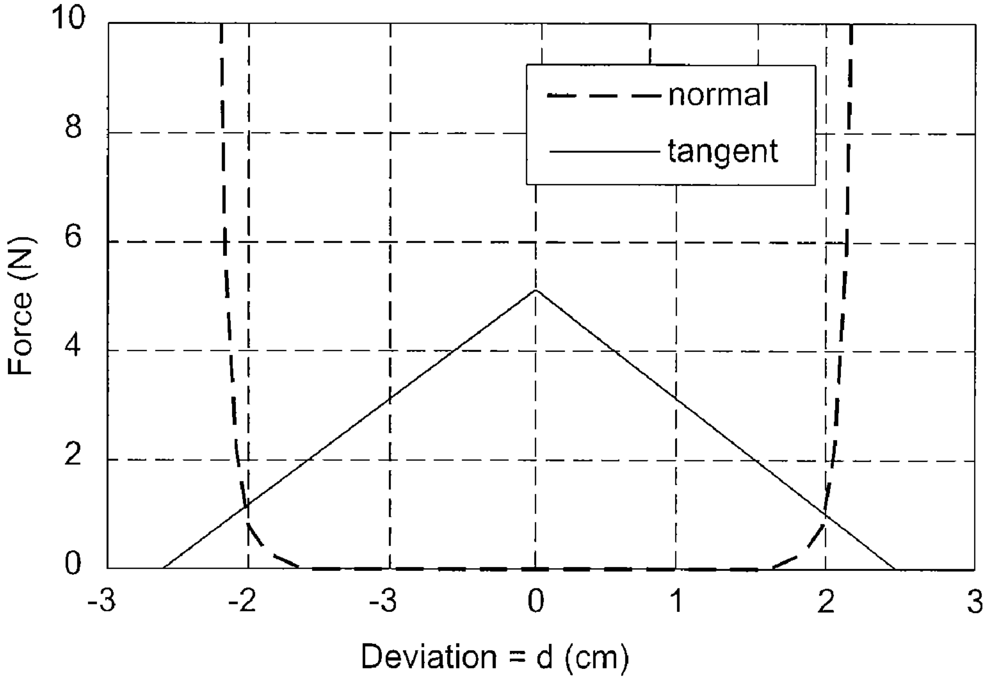
FIG. 9C is a plot of normal and tangential force profiles as a function of distance from the center of the tunnel for a relatively wide tunnel.

The shape of the tunnel is given by Eq. (5). The higher the value of n, the steeper the walls, as shown in FIG. 9A. Also, at higher values of n, the width of the tunnel gets closer to $D_n$. FIGS. 9B and 9C show exemplary plots of tangential and normal forces for relatively narrow (9B) and relatively wide (9C) virtual tunnels, as a function of distance d from the desired trajectory, where a positive force points towards the trajectory. The tangential force ramps down as the distance d increases, bringing the leg closer to the trajectory before applying tangential force.

The required actuator inputs at the leg joints that apply the above force field F is given by:

$$\tau_m=\begin{bmatrix}\tau_{m1}\\ \tau_{m2}\end{bmatrix}=J^TF+G(\theta) \tag{7}$$

where $G(\theta)$ is for gravity compensation, $\tau_m$=motor torque, and $J^T$ is a Jacobian matrix relating the joint speed to the end point speed. Finally, the forces in the linear actuators $F_m=[F_{m1}, F_{m2}]$ are computed using the principle of virtual work, given by:

$$F_{mi}=\frac{\dot{\theta}_i}{\dot{l}_i}\tau_{mi}\quad i=1,2,$$

where $I_i$ is the length if the $i^{th}$ actuator.

Simulated and Experimental results with Force Field Controller

Simulations performed using the parameters shown in FIGS. 9B and 9C showed that the error between the desired trajectory and the actual trajectory achieved was less for the relatively smaller virtual tunnel as compared to the relatively wider virtual tunnel, demonstrating that the maximum deviation of the foot from the desired trajectory can be controlled using the width of the tunnel $D_n$ as the parameter. When $K_{Ft}$ was increased and all other parameters were kept the same, the tangential forces also increased, reducing the gait cycle period, demonstrating that $K_{Ft}$ can be used as a parameter to change the gait time period.

Figure 9D:
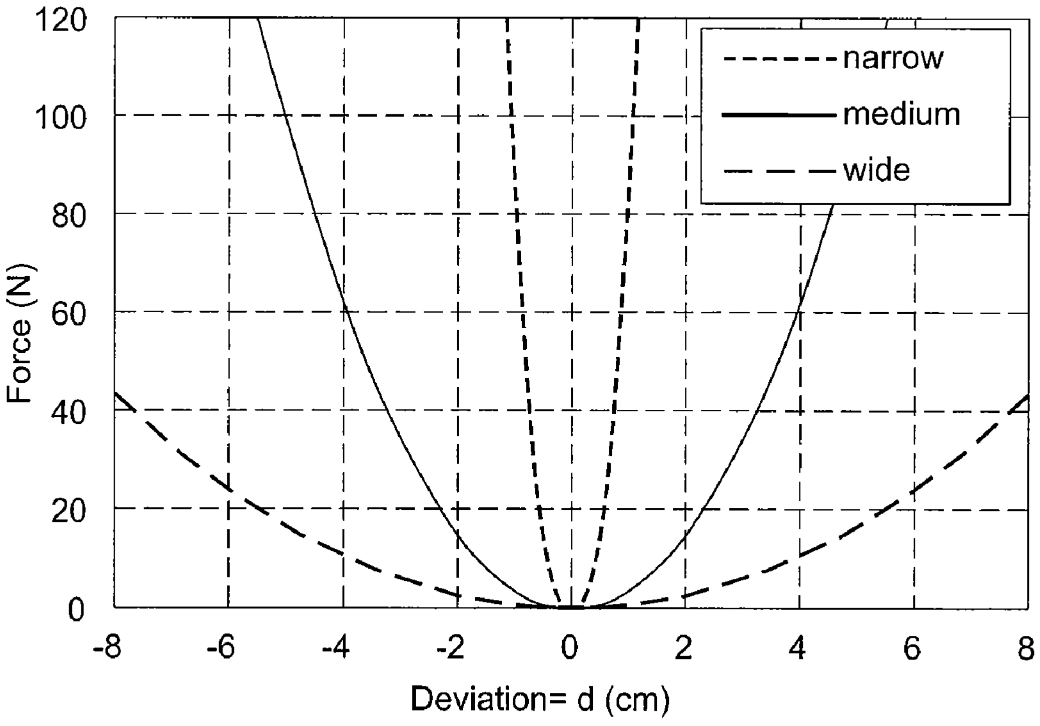
FIG. 9D is a plot of normal and tangential force profiles as a function of distance from the center of the tunnel for exemplary narrow, medium, and wide tunnels.

Experiments with the force field controller were conducted with healthy subjects in the device at three tunnel widths shown in the FIG. 9D. These results showed that as the tunnel is made narrower, the actual human gait trajectory gets closer to the desired trajectory.

Figure 10A:
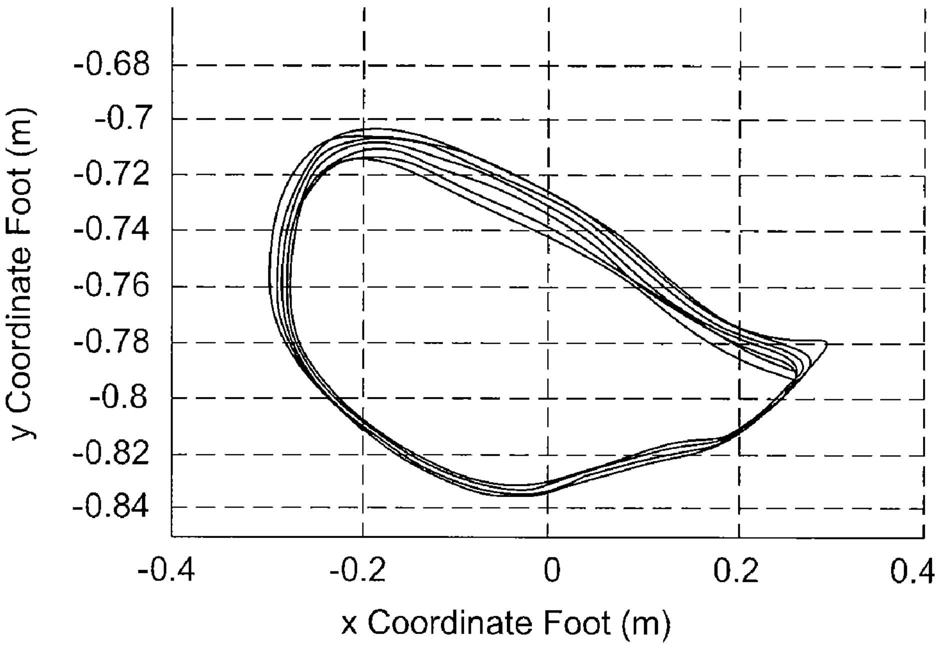
FIG. 10A is a plot of baseline actual normal gait trajectory for a human subject wearing the orthosis of FIG. 1.
Figure 10B:
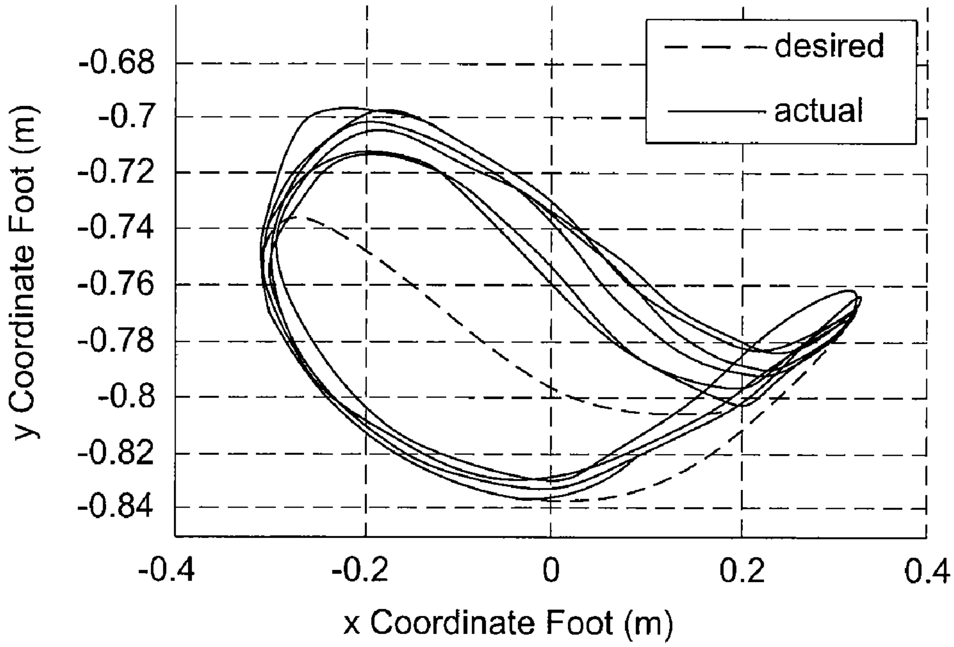
FIG. 10B is a plot of a desired trajectory of FIG. 10A rendered by distorting the baseline trajectory of FIG. 10A, along with the actual trajectory of a human subject wearing the orthosis of FIG. 1 and attempting to match the desired trajectory using only visual feedback.

The experiments involved six healthy subjects, divided into two groups, each consisting of three experimental and three control. The subjects donned the device and the joints of the machine and the human were aligned. The subjects walked on a treadmill with a speed of 2 mph and their baseline foot trajectory was recorded, as shown in FIG. 10A. A template was matched to this recorded foot trajectory and then was distorted by roughly 20% along the two Cartesian directions to generate a distorted template for the foot motion, as outlined by the dashed line in FIG. 10B.

Figure 10C:
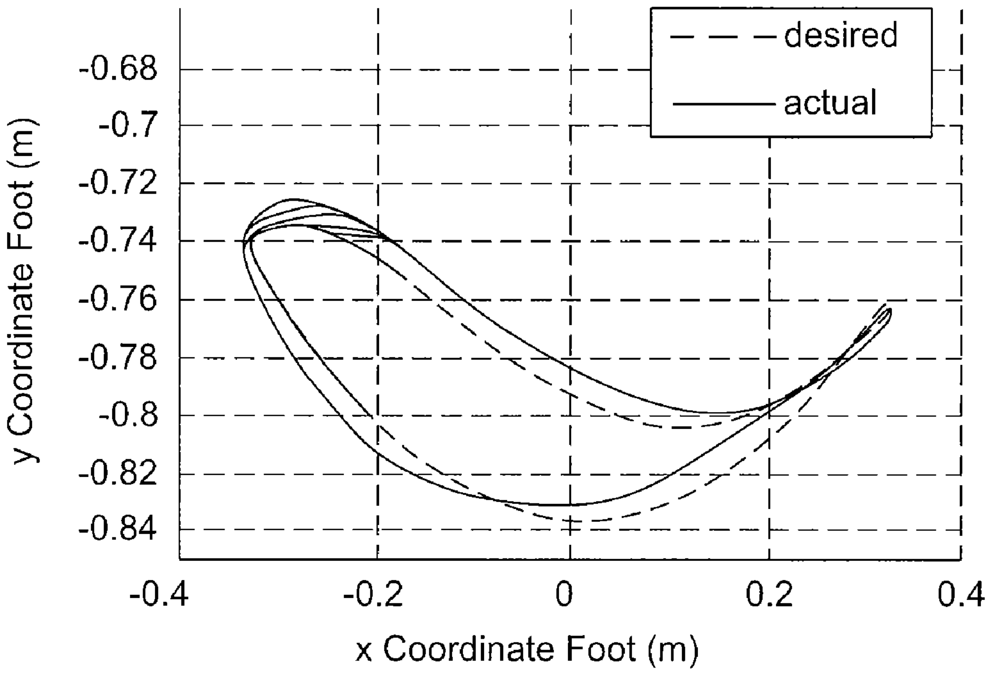
FIG. 10C is a plot of training data for a user trying to match a desired foot trajectory while wearing the orthosis of FIG. 1 using a force-field controller with a relatively narrow virtual tunnel ($D_n$=−0.003, n=1, $D_t$–1, $K_d$=−30, $K_t$=50).
Figure 10D:
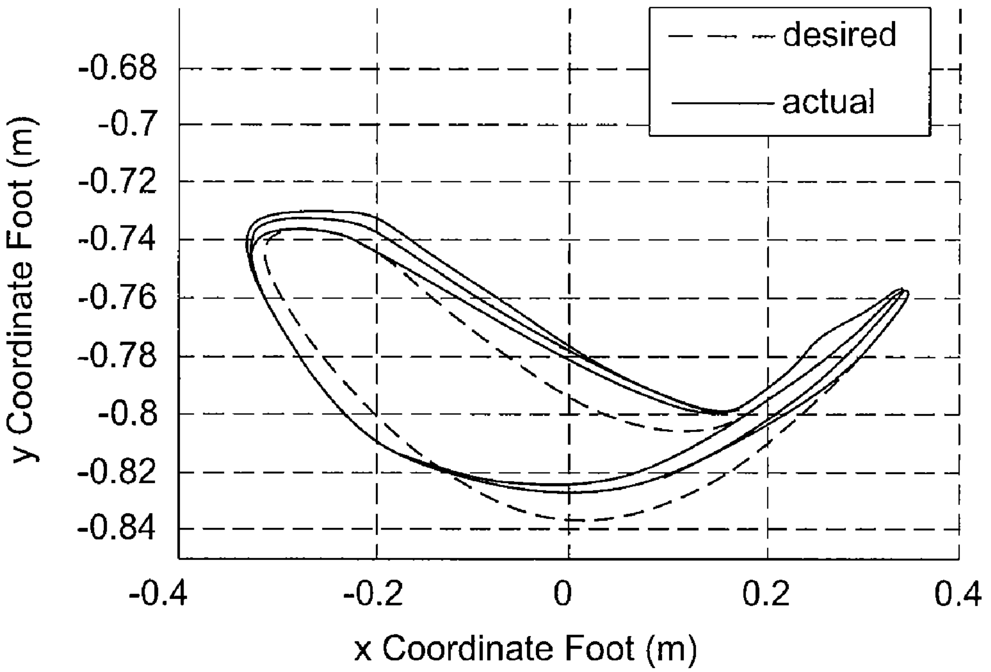
FIG. 10D is a plot of training data for a user trying to match a desired foot trajectory while wearing the orthosis of FIG. 1 using a force-field controller with the same parameters as used while generating the plot in FIG. 10C, but with a medium width virtual tunnel ($D_n$=0.006).
Figure 10E:
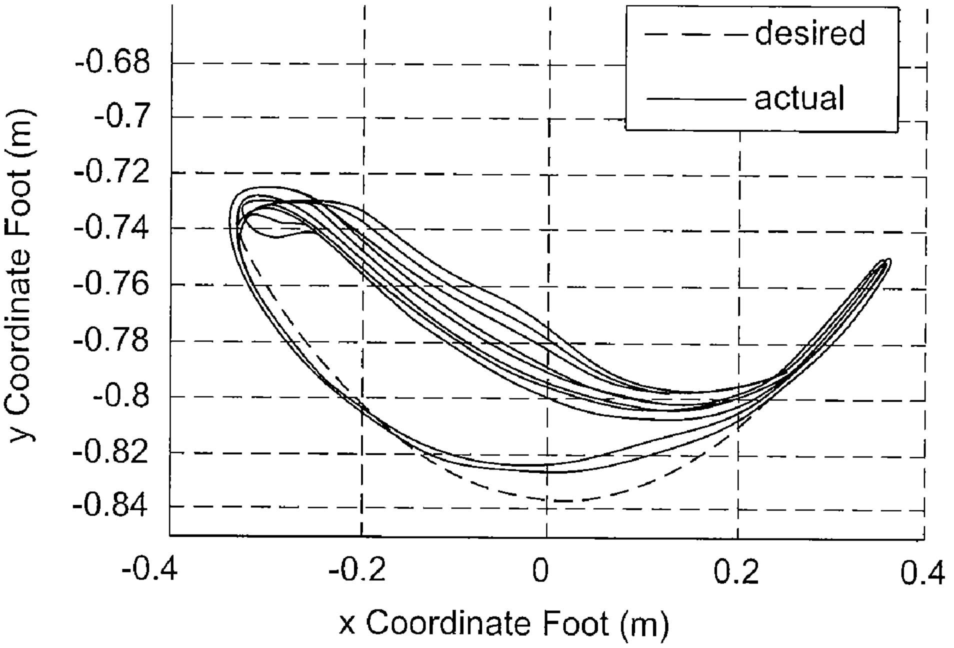
FIG. 10E is a plot of training data for a user trying to match a desired foot trajectory while wearing the orthosis of FIG. 1 using a force-field controller with the same parameters as used while generating the plots in FIGS. 10C and 10D, but with a relatively wide virtual tunnel ($D_n$=0.008).
Figure 10F:
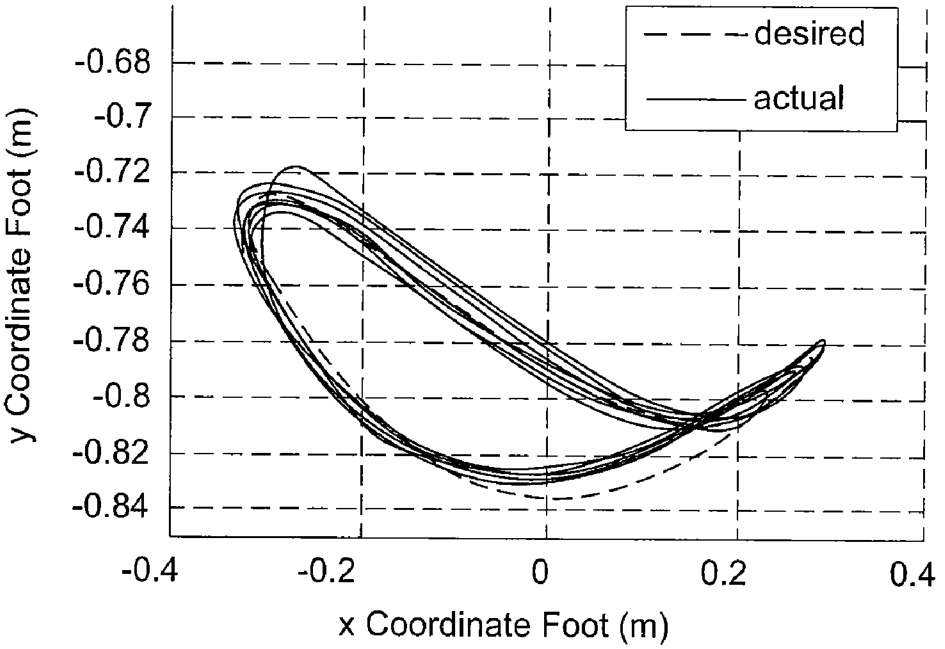
FIG. 10F is a plot of training data for a user trying to match a desired foot trajectory while wearing the orthosis of FIG. 1 using no robotic assistance and no visual assistance, after completion of training with the force-field controller.

Each subject tried to match this distorted template voluntarily for ten minutes using visual feedback of the foot trajectory. As shown by the solid lines in FIG. 10B, the subjects were not able to easily change the foot trajectory using only visual feedback. The experimental group was then given robotic training in three ten-minute sessions using narrow, wider, and widest tunnel widths, as illustrated in FIGS. 10C, 10D, and 10E. At the end of these three sessions, the robotic assistance and the visual feedback were taken away. The gait data of the subject was recorded by joint sensors on the robot. The control group practiced matching the distorted gait template over three 10 minute sessions using only visual feedback. At the end of these three sessions, the visual feedback was taken away and the foot trajectory data was recorded, as shown in FIG. 10F. This data shows that the experimental group was able to learn the distorted gait pattern using the robotic force field. Data from the control group did not show any marked learning between pre and post training data.

Various Embodiments

While the exemplary leg orthosis described herein comprises linear actuators at the hip joint and knee joint, with force-torque sensors and encoders, the invention is not limited to any particular type of actuator. Although the controllers were used with either model based or load-cell based friction compensation to make the linear actuators back-drivable, with load-cell based friction compensation being preferable, the invention is not limited to any particular type of friction compensation or method for making the actuators back-drivable. Back-drivability of the actuators is important for making the device responsive to human applied forces by not resisting the motion.

Three types of controllers are described herein for controlling the actuator: trajectory tracking PD controllers, set point PD controllers, or a force-field controllers. The set-point controller and force-field controller were found to be more desirable for training because the forces on the user do not increase if the user wishes to stop the motion of his leg. In a set-point controller, because the set-point always lies ahead of the human leg position along the trajectory by a specified amount, irrespective of the direction of motion of the leg, the interaction forces move the leg along the trajectory and do not increase in magnitude indefinitely. This feature is further augmented by the guiding nature of the tunnel walls in force-field controller. In both these controllers, the addition of damping forces in the controller makes sure that the velocities of the leg lie within safe limits. As shown in previous sections, various parameters can be chosen to apply suitable forces that can assist desirable motion and resist undesirable motion of the leg, and are suitable for rehabilitation of a lower extremity. Although three types of controllers have been described, with relative advantages of each, the invention is not limited to any particular type of controller, control methodology, or control logic.

Furthermore, while a particular leg orthosis design is described herein, the invention is not limited to any particular orthosis design, nor is it limited only to use in connection with leg orthoses. Finally, although the invention has great utility in physical therapy and rehabilitation applications, such as for assisting a patient with recovery from a stroke or other impairment, the experimental data showing the ability for healthy subjects to change their gait to mimic a programmed trajectory shows that this invention has other utility as well.

For example, the invention may be applied to athletic training, in which, for example, a runner wishes to change a small aspect of his or her stride to shave seconds off of his or her time. Using encoders in the actuators, the subject can record his or her preexisting foot trajectory while wearing the orthosis, modify stored foot trajectory data to reflect the desired trajectory, and then begin walking or running while wearing the orthosis with robotic feedback to guide the user's foot into the desired trajectory. Visual feedback can further help the user to hone his or her trajectory. The training can be continued for a sufficient amount of time and/or number of repetitions for the user to develop muscle memory for the new trajectory. Similarly, orthoses designed for other parts of the body may be used to improve the mechanics of a baseball pitch, a tennis serve, a golf swing, and the like, to name only a few of limitless examples. Furthermore, if the trajectory of a particular person is deemed to be ideal or desirable, the person with the ideal trajectory can record his or her trajectory, and that trajectory can then be used as the guide for users wishing to adopt the desired trajectory. The ideal or desirable trajectory may be proportionately or otherwise manipulated as required to account for differences in body size or structure between the user and the person with the desirable trajectory.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A powered orthosis adapted to be secured to a corresponding body portion of a user for guiding motion of the user, the orthosis comprising:

a plurality of structural members; and one or more joints adjoining adjacent structural members, each joint having one or more degrees of freedom and a range of joint angles, one or more of the joints comprising:

at least one back-drivable actuator governed by at least one joint actuator controller for controlling the joint angle, the one or more joint actuator controllers comprising force-field controllers that define a virtual tunnel for movement of the orthosis, the force-field controllers synchronized to cause the corresponding joint actuators to generate forces for assisting the user to move the orthosis at least in part under the user's power along a desired trajectory within an allowed tolerance, the generated forces comprising tangential forces along the desired trajectory and normal forces perpendicular to the trajectory, the tangential forces being inversely proportional and the normal forces being directly proportional to deviation from the desired trajectory.

2. A system for training a user to move a portion of the user's body in a desired trajectory, the system comprising
the powered orthosis of claim 1, and
a visual display configured to provide real-time visual feedback to the user showing a relationship between a desired trajectory and an actual trajectory followed by the orthosis in response to movement by the user.

3. A system for training a user to move a portion of the user's body in a desired trajectory, the system comprising
a powered orthosis adapted to be secured to a corresponding body portion of a user for guiding motion of the user, the orthosis comprising:
a plurality of structural members; and
one or more joints adjoining adjacent structural members, each joint having one or more degrees of freedom and a range of joint angles, one or more of the joints comprising:
at least one back-drivable actuator governed by at least one joint actuator controller for controlling the joint angle, the one or more joint actuator controllers comprising force-field controllers that define a virtual tunnel for movement of the orthosis, the force-field controllers synchronized to cause the corresponding joint actuators to generate forces for assisting the user to move the orthosis at least in part under the user's power along a desired trajectory within an allowed tolerance; and
a visual display configured to provide real-time visual feedback to the user showing a relationship between the desired trajectory and an actual trajectory followed by the orthosis in response to movement by the user.

4. The system of claim 3, wherein the forces generated by the joint actuators and applied to the orthosis for assisting the user are proportional to deviation from the desired trajectory.

5. The system of claim 3, wherein the applied forces comprise tangential forces along the trajectory and normal forces perpendicular to the trajectory, in which the tangential forces are inversely proportional and the normal forces are directly proportional to the deviation from the desired trajectory.

6. The system of claim 3, wherein the forces comprise damping forces.

7. The system of claim 3, wherein the orthosis is a leg orthosis comprising a frame, a trunk connected to the frame at one or more trunk joints, a thigh segment connected to the trunk at least a hip joint, and a shank segment connected to the thigh segment at a knee joint.

8. The powered orthosis of claim 7, wherein the frame is adapted to support at least a portion of the weight of the orthosis and the user.

9. The powered orthosis of claim 7, further comprising a foot segment attached to the shank segment at an ankle joint.

10. The powered orthosis of claim 7, wherein the hip joint has at least one degree of freedom in the sagittal plane governed by a first actuator and the knee joint has at least one degree of freedom governed by a second actuator.

11. The powered orthosis of claim 10, wherein the first actuator and the second actuator each comprise linear actuators having friction compensation sufficient to make the actuators back-drivable.

12. The powered orthosis of claim 7, further comprising a first connector for connecting the orthosis thigh segment to a corresponding thigh of a user and a shank connector for connecting the orthosis shank segment to a corresponding shank of a user, the first connector having a first force-torque sensor to measure net forces between the user and the orthosis, and the second connector having a second force-torque sensor to measure net forces between the user and the orthosis.

13. A method for training a user to move a portion of the user's body in a desired trajectory, the method comprising:
(a) securing the user to an orthosis comprising a plurality of exoskeletal members and a plurality of joints each having one or more degrees of freedom and a spectrum of joint angles between adjacent members connected at the joint, a plurality of the joints each comprising at least one backdrivable actuator governed by a controller for controlling the joint angle, the plurality of joint controllers synchronized with one another;
(b) causing the synchronized joint controllers to operate the corresponding actuators to generate forces for assisting the user to move the orthosis at least in part under the user's power along a desired trajectory within an allowed tolerance; and
(c) providing visual feedback to the user that shows a relationship between the desired trajectory and an actual trajectory followed by the orthosis in response to movement by the user.

14. The method of claim 13, wherein the joint controllers comprise force-field controllers that define a virtual tunnel for movement of the orthosis, the method comprising in step (b) generating forces for assisting the user that are proportional to deviation of the actual trajectory from the desired trajectory.

15. The method of claim 14, comprising generating tangential forces along the trajectory inversely proportional to the deviation from the desired trajectory and normal forces perpendicular to the desired trajectory directly proportional to the deviation from the desired trajectory.

16. The method of claim 13, wherein the orthosis comprises a leg orthosis comprising a frame adapted to support at least a portion of the weight of the orthosis and the user, a trunk connected to the frame at one or more trunk joints, a thigh segment connected to the trunk at least a hip joint, and a shank segment connected to the thigh segment at a knee joint, and a foot segment attached to the shank segment at an ankle joint, the hip joint having at least one degree of freedom in the sagittal plane governed by a first actuator and the knee joint having at least one degree of freedom governed by a second actuator, the method comprising training the user to move the user's leg in a desired gait.

17. A method for rehabilitation of a patient with impaired motor control, comprising training the user to move a portion of the user's body in a desired trajectory in accordance with the method of claim 13.

18. A method for training a healthy user to adopt a desired trajectory for a body motion, the method comprising:
(a) securing the user to an orthosis comprising a plurality of exoskeletal members and a plurality of joints each having one or more degrees of freedom and a spectrum of joint angles between adjacent members connected at the joint, a plurality of the joints each comprising at least one back-drivable actuator governed by a controller for controlling the joint angle, the plurality of joint controllers synchronized with one another;
(b) causing the synchronized joint controllers to operate the corresponding actuators to generate forces for assisting the user to move the orthosis at least in part under the user's power along the desired trajectory within an allowed tolerance; and
(c) providing visual feedback to the user that shows a relationship between the desired trajectory and an actual trajectory followed by the orthosis in response to movement by the user.

* * * * *